United States Patent
Patel (10) Patent No.: US 6,319,281 B1
(45) Date of Patent: Nov. 20, 2001

(54) ARTIFICIAL VENOUS VALVE AND SIZING CATHETER

(76) Inventor: Kumar R. Patel, 230 Sherman Ave., Glen Ridge, NJ (US) 07028

( * ) Notice: Subject to any disclaimer, the term of this patent is extended or adjusted under 35 U.S.C. 154(b) by 0 days.

(21) Appl. No.: 09/274,715

(22) Filed: Mar. 22, 1999

(51) Int. Cl.[7] ................................................. A61F 2/24
(52) U.S. Cl. ........................ 623/2.3; 600/587; 33/512
(58) Field of Search .................... 623/1.24, 1.26, 623/900, 2, 2.37; 606/198, 108, 194, 200; 600/587; 33/511, 512

(56) References Cited

U.S. PATENT DOCUMENTS

| | | |
|---|---|---|
| 953,282 | 3/1910 | Nash . |
| 1,306,391 | 6/1919 | Romanoff . |
| 1,547,668 | 10/1925 | Poltin . |
| 2,292,003 | 8/1942 | Yant et al. . |
| 2,832,078 | 4/1958 | Williams . |
| 3,113,586 | 12/1963 | Edmark, Jr. . |
| 3,661,148 | 5/1972 | Kolin . |
| 3,839,741 * | 10/1974 | Haller ............................................. 3/1 |
| 3,859,668 | 1/1975 | Anderson . |
| 4,086,665 * | 5/1978 | Poirier ........................................ 623/1 |
| 4,328,811 | 5/1982 | Fogarty . |
| 4,602,911 * | 7/1986 | Ahmadi et al. ............................ 623/2 |
| 4,643,194 | 2/1987 | Fogarty . |
| 4,851,001 | 7/1989 | Taheri . |
| 4,878,909 | 11/1989 | Parravacini . |
| 4,904,254 | 2/1990 | Lane . |
| 4,932,965 | 6/1990 | Philips . |
| 5,010,892 | 4/1991 | Colvin et al. . |
| 5,042,161 | 8/1991 | Hodge . |
| 5,116,564 * | 5/1992 | Jansen et al. ............................. 623/1 |
| 5,139,515 | 8/1992 | Robicsek . |
| 5,147,389 | 9/1992 | Lane . |
| 5,156,621 | 10/1992 | Navia et al. . |
| 5,163,953 * | 11/1992 | Vince ......................................... 623/2 |
| 5,171,248 | 12/1992 | Ellis . |
| 5,326,372 * | 7/1994 | Mhatre et al. ............................. 623/2 |
| 5,397,351 * | 3/1995 | Pavcnik et al. ........................... 623/1 |
| 5,413,599 | 5/1995 | Imachi et al. . |
| 5,471,756 | 12/1995 | Bolanos et al. . |
| 5,500,014 | 3/1996 | Quijano et al. . |
| 5,518,026 | 5/1996 | Benjey . |
| 5,562,617 | 10/1996 | Finch, Jr. et al. . |
| 5,607,465 | 3/1997 | Camilli . |
| 5,607,471 | 3/1997 | Seguin et al. . |
| 5,665,116 | 9/1997 | Chaisson et al. . |
| 5,713,953 | 2/1998 | Vallana et al. . |
| 5,716,417 | 2/1998 | Girard et al. . |
| 5,741,328 | 4/1998 | Reif . |
| 5,766,240 * | 6/1998 | Johnson ..................................... 623/2 |
| 5,814,098 * | 9/1998 | Hinnenkamp et al. .................. 623/2 |
| 5,840,081 | 11/1998 | Anderson et al. . |
| 5,855,601 | 1/1999 | Bessler et al. . |
| 5,925,063 * | 7/1999 | Khosravi ............................... 606/200 |
| 5,957,949 | 9/1999 | Leonhardt et al. . |
| 5,984,959 | 11/1999 | Robertson et al. . |
| 6,013,019 * | 1/2000 | Fischell et al. ........................... 600/3 |
| 6,102,945 * | 8/2000 | Campbell ............................ 623/2.37 |

OTHER PUBLICATIONS

Carbomedics The Heart Valve Company, Carbomedics, Inc.

\* cited by examiner

*Primary Examiner*—Cary E. O'Connor
(74) *Attorney, Agent, or Firm*—Rosenman & Colin LLP (57) ABSTRACT

A valve device for use in a body cavity. The device including a valve ring having a compressible diameter. Further, leaflets are pivotally disposed within the valve ring for movement from an open position to a closed position. A catheter device including a first catheter and a second catheter disposed within the first catheter. The first catheter includes an expandable member disposed at a lower end. The device also includes a scale. The second catheter being advanced within the first catheter causes the expandable member to move to an expanded position, which corresponds to a diameter measurement on the scale.

27 Claims, 7 Drawing Sheets

ARTIFICIAL VENOUS VALVE AND SIZING CATHETER

BACKGROUND OF THE INVENTION

1. Field of the Invention

The present invention relates in general to medical valve devices, in particular, to an artificial valve that is readily percutaneously inserted into a vein, as well as implanted into a prosthetic graft to be used for a bypass in the venous system. Further, the present invention relates in general to catheter devices, in particular, to a catheter device capable of measuring an internal diameter of a body cavity such as an artery or vein, as well as for measuring the internal diameter of other tubular structures such as a bile duct, bronchus or ureter.

2. Description of Prior Developments

Progress in surgery for venous disease has lagged far behind developments in other areas such as arterial surgery. The propulsive force of the left ventricle of the heart makes the arterial tree a high pressure and high velocity system. In contrast, the venous system is characterized by low pressure and low velocity. Effective venous return is dependent on the functioning of venous valves, patency of veins and the contraction of the peripheral muscles, known as the "venous pump".

Valvular incompetence occurs when the natural venous valves do not function properly. This can be either congenital or acquired. When valves become incompetent, the direction of blood flow in a vein is reversed due to the effect of gravity, increased pressure within the abdominal cavity, or other conditions causing venous compression. Acquired incompetence is usually a consequence of venous thrombosis, which is when a blood clot forms in a vein. Thrombosis is followed by formation of fibrous tissue, which destroys the normal structure and function of the valves, causing valvular incompetence and venous insufficiency.

Loss of venous patency, i.e., venous thrombosis or obstruction, results from conditions such as stasis, reduced blood volume, injury to the inner lining of the vein, extrinsic compression and thrombotic disorders. Although, an obstruction theoretically can be corrected by a bypass, venous bypasses are rarely performed and are often unsuccessful.

Valvular incompetence and venous obstruction, alone or in combination, lead to chronic venous insufficiency. This often causes permanent disability due to pain, swelling, and ulceration of the lower limbs, and places the patient at high risk for recurrent thrombosis and pulmonary embolism. Treatment is difficult, prolonged, and often unsuccessful. These patients require home care, frequent office visits, and intermittent hospitalization. Consequently, millions of dollars are spent each year for the care of these patients.

Valvular incompetence previously has been treated by a number of procedures including the direct repair of incompetent valves, vein transfer, vein segment transfer, or venous bypass using a competent valve. A vein transfer involves the surgical transfer of a vein with incompetent valves to one with normally functioning valves. A vein segment transfer involves transferring a vein segment with a normal valve to other veins with defective valves. However, these procedures are rarely performed since such procedures are usually only applicable to a limited number of patients. Moreover, these operations are technically difficult to perform and the results are poor.

Chronic venous obstruction has previously also been treated by other procedures including an autogenous vein bypass and a prosthetic graft bypass. However, these procedures have also been found to be less than satisfactory since both can only be used in a few select cases with limited success.

In particular, the autogenous vein bypass often fails since it provides too small a caliber for bypassing large veins and insufficient length to bypass the obstructed segment. The prosthetic graft bypass is rarely used since it has a high incidence of thrombosis or clotting. Further, all prosthetic grafts are inherently incompetent since there are no valves in the grafts.

Another possible alternative for treating valvular incompetence would be to replace the defective natural valve with an artificial valve. The use of artificial valves is well known in other areas of the vascular system such as the heart. However, these valves are not adaptable to veins due to a number of unique requirements. For example, a venous valve would have to be designed to operate in a low pressure and low flow system. Further, a venous valve would have to be smaller in diameter and reinforced to prevent being compressed by outside forces.

Although, artificial venous valves have not been used in patients so far, the prior art does include a number of such devices. For example, U.S. Pat. No. 4,851,001 to Taheri, issued Jul. 25, 1989, and U.S. Pat. No. 5,607,465 to Camilli, issued Mar. 4, 1997, both disclose an artificial valve for use in blood vessels. However, the valve devices disclosed in these patents have a number of problems. For example, such devices are not generally readily percutaneously inserted into a blood vessel. Further, such devices generally make no provision for measuring the internal diameter of the vein at the proposed site of placement.

However, the prior art does disclose the devices for measuring internal diameters. For example, U.S. Pat. No. 3,661,148 to Kolin, issued May 9, 1972, and U.S. Pat. No. 5,010,892 to Colvin et al., issued Apr. 30, 1998, discloses such devices.

However, in regard to veins such devices have problems. For example, such devices do not directly measure the internal diameters. Such devices are also not specifically intended for use in blood vessels. Further, such devices are not versatile enough to perform other functions.

SUMMARY OF THE INVENTION

The present invention has been developed to fulfill the needs noted above and therefore has an object to provide an artificial valve that is appropriate for the diameter of the body cavity (vein) or a prosthetic graft used for a venous bypass.

Another object of the invention is to provide an artificial valve that is readily percutaneously inserted into a patient, thereby eliminating the need for an incision, operation, and major anesthesia.

Another object of the invention is to provide an artificial valve that does not require suturing.

Another object of the invention is to provide an artificial valve that is fabricated from non-thrombogenic material.

These and other objects are met in accordance with the present invention which is directed to a valve device including a valve ring having a compressible diameter, which enables the valve device to be compressed during introduction into the vein. Further, leaflets are pivotally disposed within the valve ring for movement from an open position to a closed position.

The valve ring includes a first plurality of arcuate tubes and a second plurality of arcuate tubes telescopically disposed in the first tubes. A spring is disposed in each of the first tubes between two of the second tubes. Further, projections extend away from each end of the second tubes and a lip is included on each end of the first tubes. The springs maintain the valve ring in an extended position in the absence of an external force. The projections prevent disconnection of the first and second tubes.

The present invention has also been developed to fulfill the needs noted above and therefore has an object to provide a catheter device that is capable of accurately measuring an internal diameter of a body cavity such as a vein or artery.

Another object of the invention is to provide a catheter device that is versatile enough to perform other functions such as adjunctive angiography and the introduction of irrigating solutions.

Another object of the invention is to provide a catheter device that is readily percutaneously inserted into a patient.

These and other objects are met in accordance with the present invention which is directed to a catheter device including a first catheter and a second catheter disposed within the first catheter. The first catheter includes an expandable member disposed at a lower end. The second catheter being advanced within the first catheter causes the expandable member to move to an expanded position, which corresponds to a diameter measurement on the scale located near the upper end of the second catheter.

The expandable member has a cylindrical configuration, which includes separate plates attached to the lower end of the first catheter. A spring is disposed around the outer edges of the plates in order to maintain the plates in an unexpanded position when the second catheter is not being advanced. The outer edges of the plates include a groove in order to receive the spring.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawings, like reference characters designate like parts.

DETAILED DESCRIPTION OF THE PREFERRED EMBODIMENTS

Figure 1:
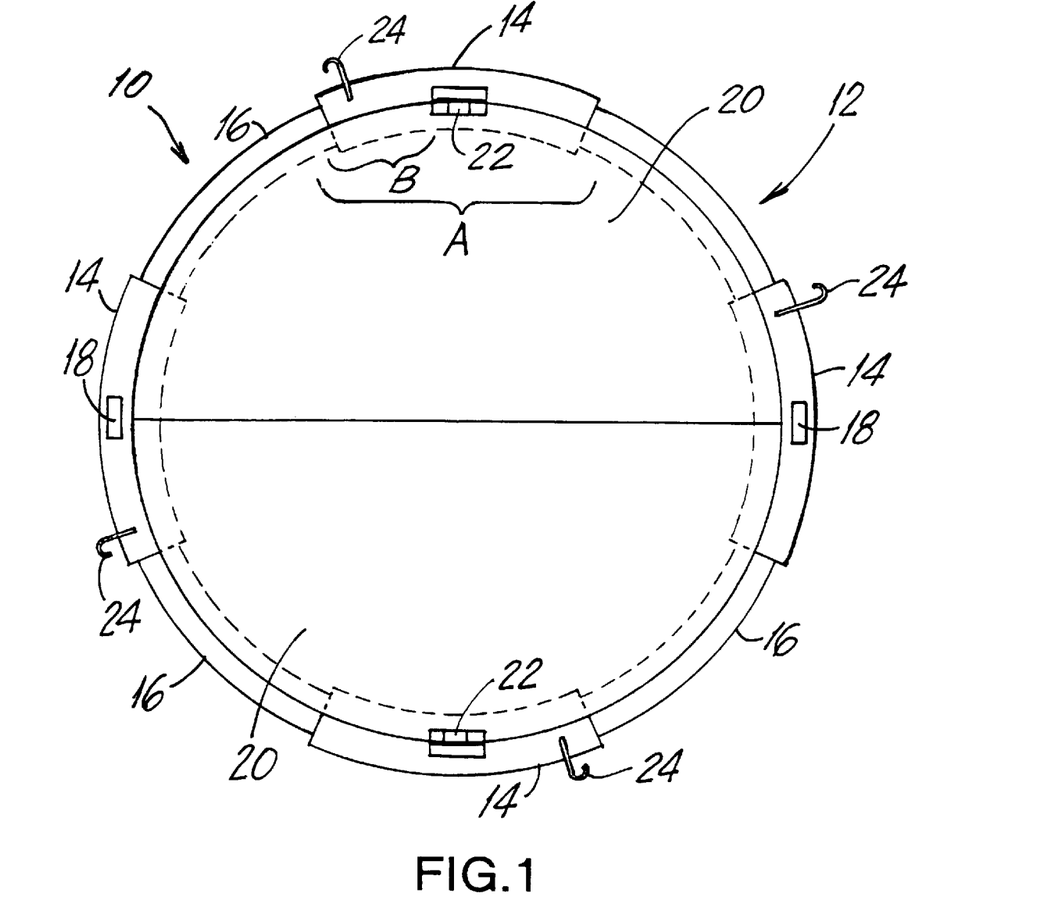
FIG. 1 is a top view of the venous valve according to the present invention.
Figure 4:
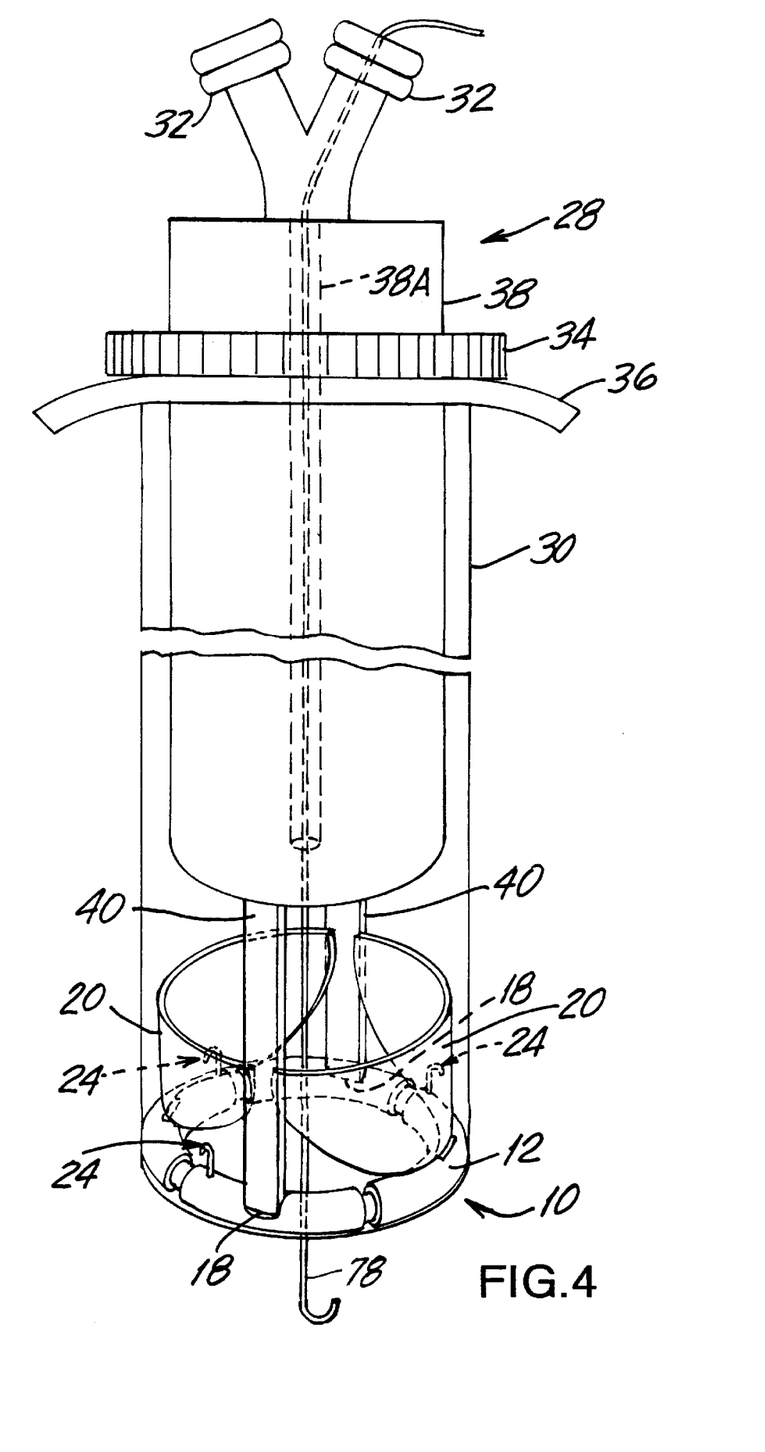
FIG. 4 is a view of the venous valve loaded in a valve carrier according to the present invention.

In conjunction with the drawings beginning with FIG. 1, an embodiment of the venous valve 10 according to the present invention is shown. The venous valve 10 includes a valve ring 12 that has a compressible diameter. This enables the valve ring 12 to be compressed from an extended position to a smaller diameter, which allows the venous valve 10 to be loaded into the valve carrier as shown in FIG. 4.

The compressibility of the valve ring 12 is a significant feature of the present invention since it permits percutaneous insertion of the venous valve eliminating the need for operation. Percutaneous insertion is when an object is inserted through a skin puncture instead of by an incision. In addition, percutaneous insertion is performed under local anesthesia, eliminating the need for (and, therefore, avoiding the complications of) regional or general anesthesia.

According to the present invention, the venous valves 10 are made in a range of different sizes. After measuring the diameter of the vein at the proposed site of valve placement, an appropriately sized valve is selected for placement.

As can be seen from FIG. 1, the valve ring 12 includes a first plurality of arcuate tubes 14 and a second plurality of arcuate tubes 16. The second tubes 16 have a diameter slightly smaller than the diameter of the first tubes 14, which enable the second tubes 16 to be telescopically disposed within the first tubes 14, as shown. The second tubes 16 being moved in and out of the first tubes 14 enables the diameter of the valve ring 12 to be made smaller and larger, respectively.

It is preferred that the first and second tubes 14,16 are fabricated from a flexible non-thrombogenic material such as stainless steel or titanium. The use of a non-thrombogenic material is desirable since it will prevent the production of blood clots that potentially could clog the venous valve 10 when placed within a vein of a patient.

According to the present invention, it is also preferred that the valve ring 12 will statically remain in the extended position, as shown. In order to keep the valve ring 12 extended with no force applied, each of the first tubes 14 include a spring, which will be described in detail hereinafter.

In order to compress the valve ring 12 from the extended position, a radial force must be applied to counter the force of the springs. In order to enable the application of such a force, slots 18 are provided on the valve ring 12. The application of a radial force to the slots 18, using a forceps or clamp, will cause the valve ring 12 to be compressed from the extended position.

The venous valve 10 also includes leaflets 20, which are pivotally connected to the valve ring 12 by hinges 22. As can be seen, the leaflets 20 are in a closed position parallel to the plane of the valve ring 12. However, when a force is applied to the bottom surfaces of the leaflets 20, the leaflets 20 will pivot upward around the hinges 22 enabling fluid to flow through the valve ring 12.

According to the present invention, it is preferred that the leaflets 20 are each attached to the valve ring 12 by a single hinge 22. Further, it is preferred that the leaflets 20 are also fabricated from a semi-flexible non-thrombogenic material such as stainless steel or titanium.

The venous valve 10 also includes barbs 24. The barbs 24 are oriented in a plane perpendicular to the plane of the valve ring 12 when the venous valve 10 is within the valve carrier as shown in FIG. 4. Before the venous valve 10 is loaded within the valve carrier, the barbs 24 project slightly outside the periphery of the valve ring 12. When the venous valve 10 is released within a vein of a patient, the barbs 24 spring outwards and engage the wall of the vein in order to secure the valve 10 in a particular location within the vein. Thus, the barbs 24 eliminate the need for suturing the valve in place, which was required in regard to other prior art valves. According to the present invention, it is also preferred that the barbs 24 are fabricated from a semi-rigid metal such as stainless steel.

Figure 2:
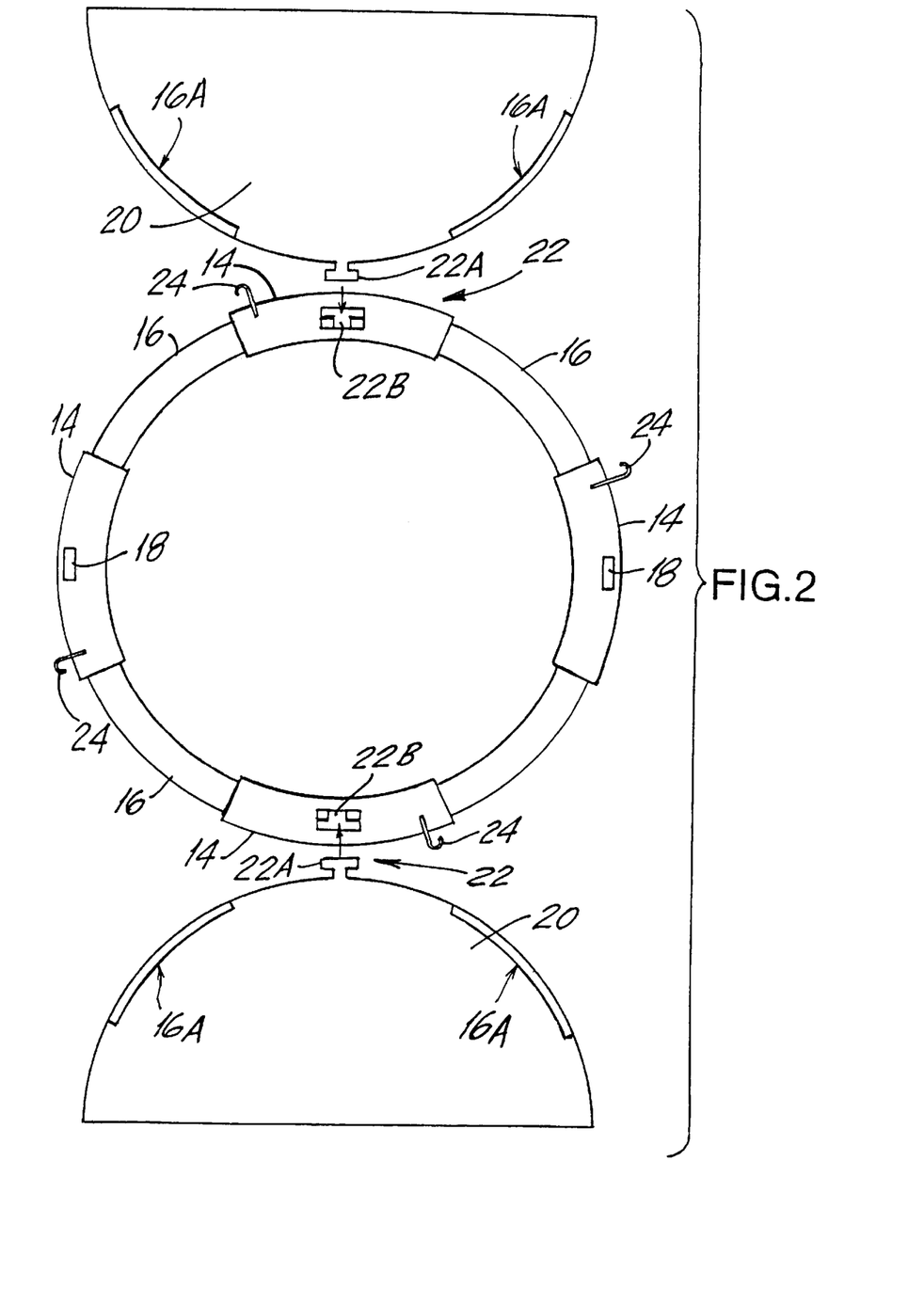
FIG. 2 is a partial exploded assembly view of the venous valve according to the present invention.

A partial exploded assembly view of the venous valve 10 according to the present invention is shown in FIG. 2. As can be seen, there are two ridges 16A located on the underside of each of the valve leaflets 20. When the valve 10 is closed, the ridges 16A lie directly over the second tubes 16. The ridges 16A compensate for the smaller diameter of the second tubes 16 by providing a seal between the leaflets 20 and the second tubes 16 when the valve 10 is closed.

The details of the hinges 22 are also shown. Each of the hinges 22 include a T-shaped portion 22A attached to the leaflets 20 and a slotted portion 22B included on the valve ring 12. The T-shaped portion 22A is adapted to be placed within the slotted portion 22B in order to pivotally connect the leaflets 20 to the valve ring 12, as previously described.

Segment views of the adjustable valve ring 12 according to the present invention are shown in FIGS. 3A–3E. As can be seen from FIGS. 3A–3B, a spring 26 is included in each of the first tubes 14 disposed between two of the second tubes 16. As previously described, the springs 26 keep the valve ring 12 in the extended position when a compressing force is not applied.

Figure 3A:
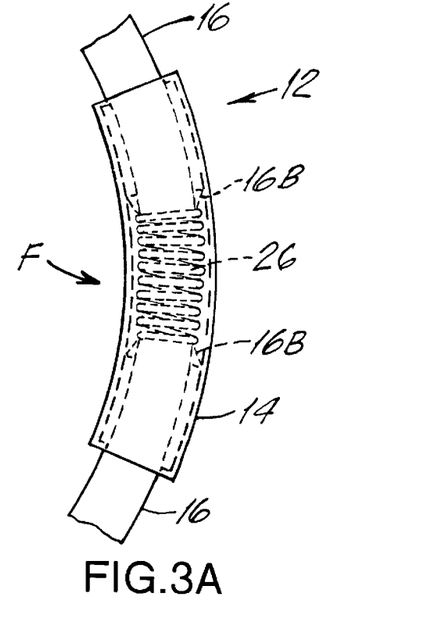
FIGS. 3A–3B are views of segment A of the valve ring shown in FIG. 1.
Figure 3B:
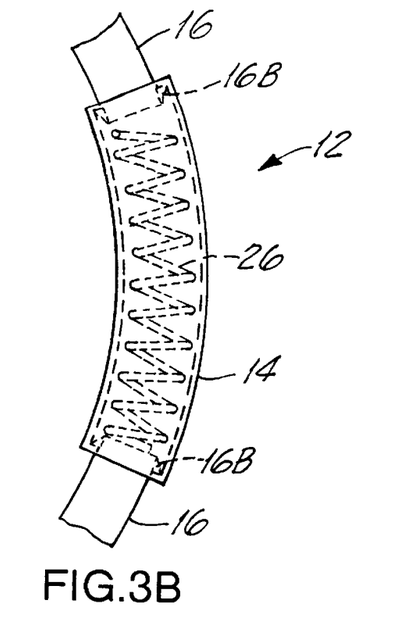

In FIG. 3A, the valve ring 12 is shown in a compressed position, where a force (F) is being applied. When the valve ring 12 is in the extended position, the force (F) being applied causes each of the second tubes 16 to move inward to compress the spring 26, as shown. When the valve 10 is released in a vein, the springs 26 cause the valve ring 12 to move to the extended position, as shown in FIG. 3B.

Figure 3C:
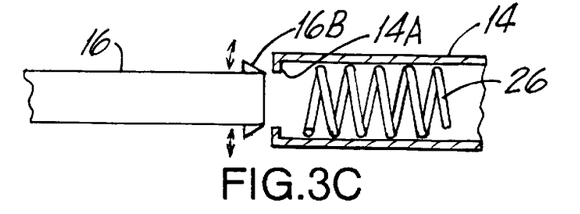
FIGS. 3C–3E are views of segment B of the valve ring shown in FIG. 1.

As can be seen from FIG. 3C, spring loaded projections 16B are included on each end of the second tubes 16. Further, a lip 14A, as shown in FIG. 3E, also extends inward at each end of the first tubes 14. The projections 16B and lips 14A prevent disconnection of the first and second tubes 14,16 while permitting compression of the valve ring when an external radial force is applied to overcome the resistance of the springs 26.

Figure 3D:
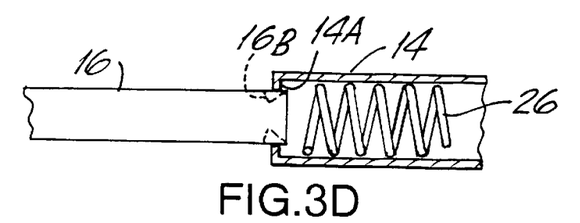
Figure 3E:
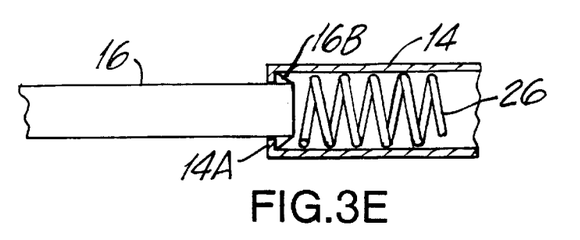

As can be seen from FIG. 3D, the projections 16A pressed inward enables the ends of the second tube 16 to fit within the lips 14A of the first tube 14. Once the ends of the second tube 16 is inside the first tube 14, the projections 16B engage the lip 14A, as shown in FIG. 3E, in order to maintain the extended position of the valve ring when no external force is applied. However, the projections 16B are configured to enable free inward movement of the second tubes 16, when such a force is applied.

A view of the venous valve 10 loaded in a valve carrier 28 according to the present invention is shown in FIG. 4. It is preferred that the valve 10 is pre-loaded in the factory. In order to load the venous valve 10 in the valve carrier 28, the valve ring 12 must be compressed and the barbs 24 pushed inward towards the center of the valve ring 12.

The barbs 24 preferably being fabricated from a semi-rigid metal, enables the barbs 24 to be bent inward and spring back to the normal position when the venous valve 12 is released from the valve carrier 28.

Further, the leaflets 20 also are pivoted upward perpendicular to the valve ring 12. The leaflets also are bent inward in order to fit within the perimeter of the compressed valve ring 12, as shown. The leaflets 20 being connected to the valve ring 12 by a single hinge enables the leaflets 20 to be bent inward. The leaflets 20 are also made of semi-rigid metal allowing them to spring back to the normal flat configuration when the valve 10 is released from the valve carrier 28.

The valve carrier 28 includes a catheter 30, which should be long enough to reach from the site of percutaneous insertion to the proposed site of valve placement in the vein. A plunger 38 is included in the top portion of the catheter 30, which provides the force to expel the venous valve 10. The plunger 38 includes a hollow bore 38A connected to a pair of ports 32 located at the top of the plunger 38, which enable flushing or, if needed, injection of angiographic dye.

The valve carrier 28 also includes a curved handle 36, which provides a grip for fingers when pressing on the plunger 38. A safety screw 34 is disposed over the handle 36. When tightened, the safety screw 34 prevents movement of the plunger 38 and thus prevents the venous valve 10 from being accidentally expelled. Connected to the lower end of the plunger 38 are bars 40, which are disposed in slots 18 of the venous valve 10. The bars 40 keep the venous valve 10 in the lower portion of the catheter 30 and also expel the venous valve 10 when the plunger 38 is depressed. In order to release the venous valve 10 into a particular location of a vein, the plunger is depressed and the bars move downward expelling the valve 10 from the catheter 30.

Once the valve 10 is released within the vein, the barbs 24 will spring outward while the valve ring 12 expands from the compressed position. When the valve ring 12 expands to the internal diameter of the vein, the barbs 24 will be embedded in the wall of the vein securing the venous valve 10 in that particular location. In addition, the valve leaflets 20 will spring back to their normal flat configuration.

The venous valve 10 according to the present invention can provide a number of benefits. First of all, since the venous valve 10 can be made in various sizes, it can be used in veins of any size. The use of this device according to the present invention, is applicable to almost all of the patients with significant valvular incompetence or venous obstruction, and reduces incidences of thrombosis by restoring normal effective venous return.

The progression of chronic venous insufficiency is prevented by restoring normal valvular function, thereby eliminating distal venous hypertension. The above-described benefits could provide a major reduction in health care costs.

Further, the venous valve 10 according to the present invention can also be used in a prosthetic graft for a venous bypass. Since the diameter of the graft is known, sizing is not necessary. One or more valves can be placed using the valve carrier at desired locations in the graft prior to the performance of the anastomoses. Valve competence can easily be confirmed by injecting normal saline into the graft before placement.

Figure 5:
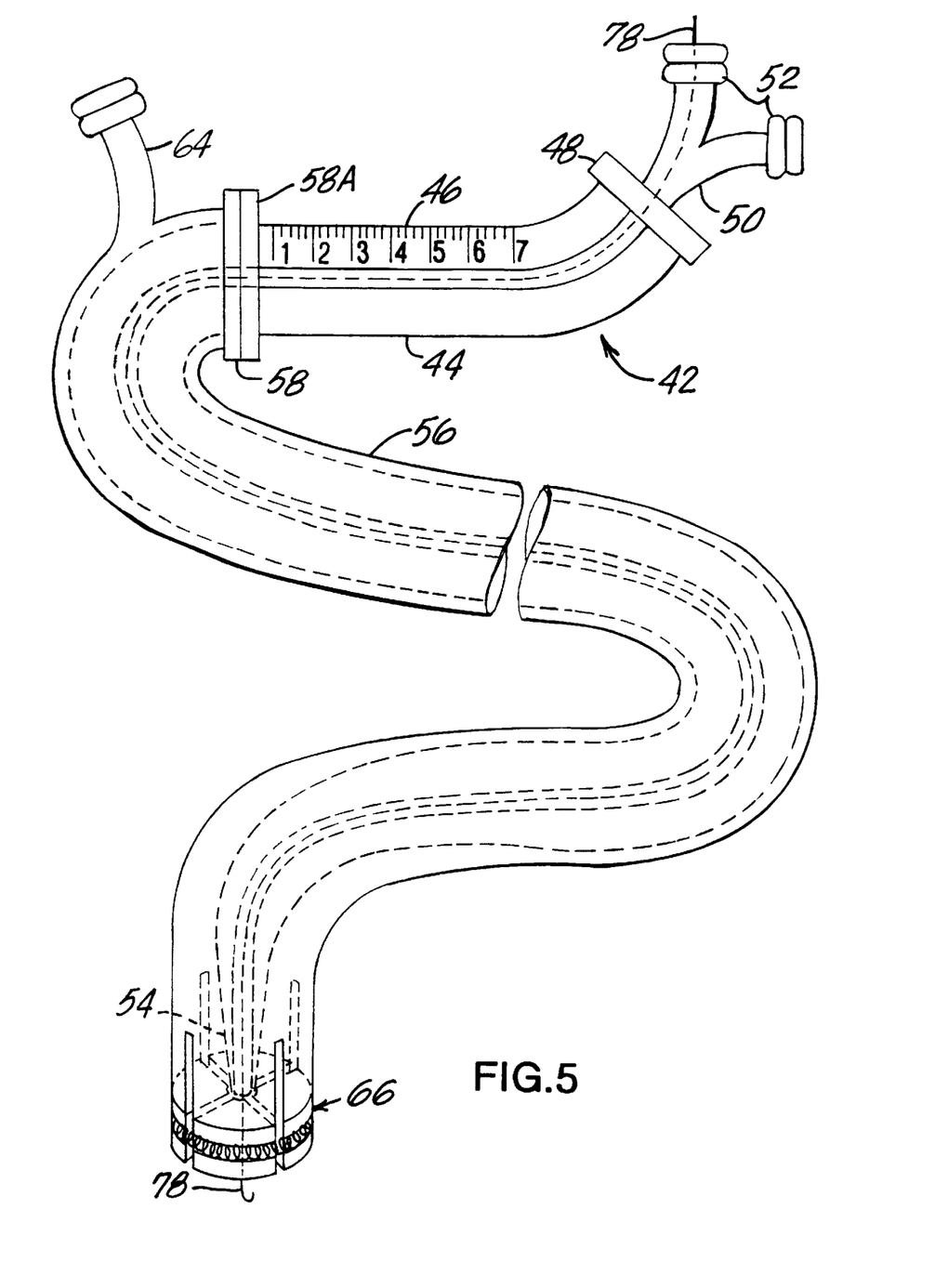
FIG. 5 is a perspective view of the sizing catheter according to the present invention.

In conjunction with the drawings beginning with FIG. 5, an embodiment of the sizing catheter 42 according to the present invention is shown. The sizing catheter 42 is configured to accurately measure the internal diameter of a body cavity such as a vein or artery, which would be useful in a variety of procedures. The sizing catheter may also be used to measure the internal diameter of other tubular structures such as a bile duct, bronchus, or ureter.

According to the present invention, it is also contemplated that that the sizing catheter 42 would be constructed in two different sizes. A smaller version of the sizing catheter 42 would have a scale in millimeters and be utilized to measure the diameter of smaller veins such as saphenous or popliteal, or smaller arteries. The larger version of the sizing catheter 42 would have a scale in centimeters and be utilized to measure larger veins such as femoral, iliac, or vena cava, or larger arteries.

Further, the sizing catheter 42 is also versatile enough to perform other functions such as adjunctive angiography and the infusion of fluids. In order to perform these functions, the sizing catheter can be inserted in the subject either percutanously through the skin or through an open blood vessel during an operation.

As can be seen from FIG. 5, the sizing catheter 42 includes an inner catheter 44 and an outer catheter 56. Both the inner and outer catheter 44,56 should be long enough so that a majority of the patient's body can be reached when the sizing catheter 42 is percutaneously inserted. Further, the inner catheter 44 should be of a diameter to enable it to be freely advanced within the outer catheter 56.

The inner catheter 44 includes a scale 46, which indicates the diameter of the body cavity being measured. In this particular embodiment, the scale 46 is disposed on an upper-outer surface of the inner catheter 44. However, the present invention contemplates placement of the scale in other locations within the device. As previously described, the scale 46 can either be in millimeters or centimeters depending on the size of the cavity being measured.

At the upper end of the inner catheter 44 are ports 52, which are utilized to pass a guide wire 78 as well as for flushing or adjunctive angiography. The ports 52 are connected to the upper end of the inner catheter 44 by a neck 50 and a cylindrical fitting 48. The cylindrical fitting 48 also provides additional rigidity to the inner catheter 44. The inner catheter 44 also includes a tapered lower end 54, which has an elongated conical shape.

The outer catheter 56 includes a cylindrical fitting 58 at the upper end. The cylindrical fitting 58 also provides additional rigidity to the outer catheter 56. Further, the cylindrical fitting 58 also includes an opening that enables the inner catheter 44 to be inserted and advanced within the outer catheter 56, which will be described in detail later.

A port 64 is also included on the outer catheter 56, which can be used for flushing. If required, the port 64 also can be utilized to inject angiographic dye.

At the lower end of the outer catheter 56 is disposed an expandable member 66. The expandable member 66 is the part that actually measures the internal diameter of the body cavity. In order to perform this measurement, the inner catheter 44 is advanced within the outer catheter 56 so that the tapered end 54 reaches the expandable member 66, as shown.

If the inner catheter 44 is further advanced, the tapered end 54 causes the expandable member 66 to expand outward, which corresponds to a diameter measurement in the scale 46. Since the tapered end 54 has an elongated conical shape, the expandable member 66 gradually expands outward providing a more accurate measurement. At the point where the side surface of the expandable member 66 contacts the inner wall of the vein, there is resistance to further advancement of the inner catheter 44. At this point the diameter of the vein is indicated on the scale 46.

Figure 6:
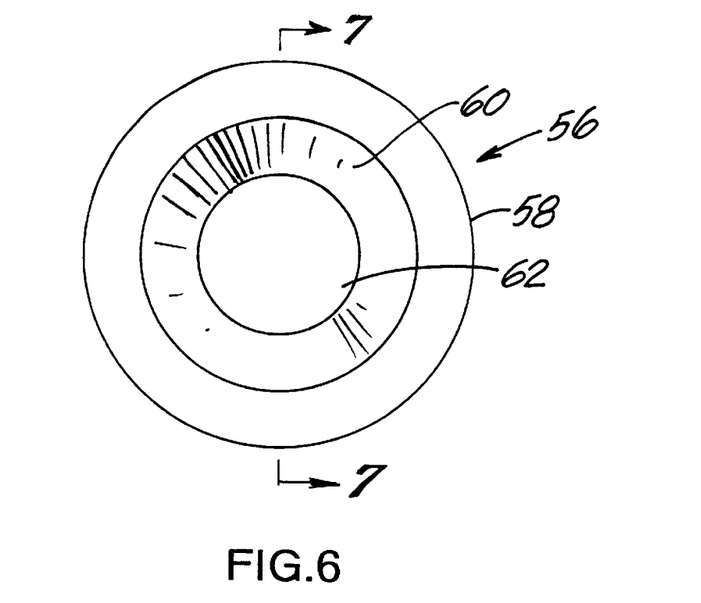
FIG. 6 is a top view of the cylindrical fitting of the outer catheter according to the present invention.

A top view of the cylindrical fitting 58 of the outer catheter 56 according to the present invention is shown in FIG. 6. Attached to an inner surface of the cylindrical fitting 58 is a diaphragm 60, which is preferably fabricated from a soft resilient material such as rubber or the like. The diaphragm 60 includes an opening 62, which as previously described enables the inner catheter 44 to be inserted and advanced within the outer catheter 56.

Figure 7:
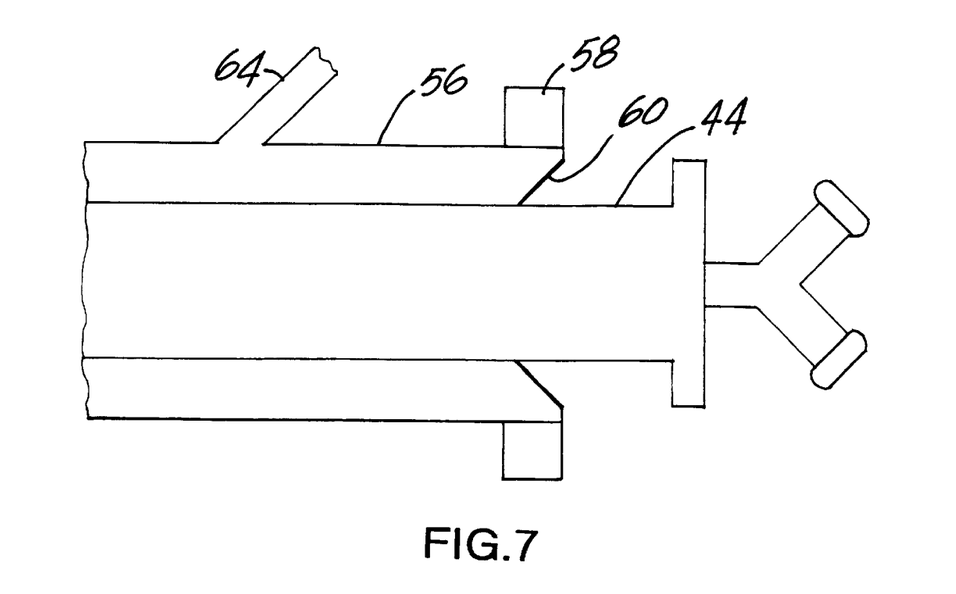
FIG. 7 is a cross-sectional view of the upper end of the sizing catheter according to the present invention.

The opening 62 should be of a diameter so that the diaphragm 60 fits tightly around the inner catheter 44 when inserted within the outer catheter 56, as shown in FIG. 7. Therefore, the diaphragm 60 provides a fluid tight seal between the catheters 44,56.

Further, the diaphragm 60 also functions to secure the inner catheter 44 within the outer catheter 56 in order to prevent slipping. The diaphragm 60 fitting tightly around the inner catheter 44 applies a frictional force to the outer surface of the inner catheter 44, which holds the inner catheter 44 in place. The frictional force is only overcome when a user applies a force in order to advance or withdraw the inner catheter 44 within the outer catheter 56. Therefore, the inner catheter 44 is prevented from slipping.

Figure 8:
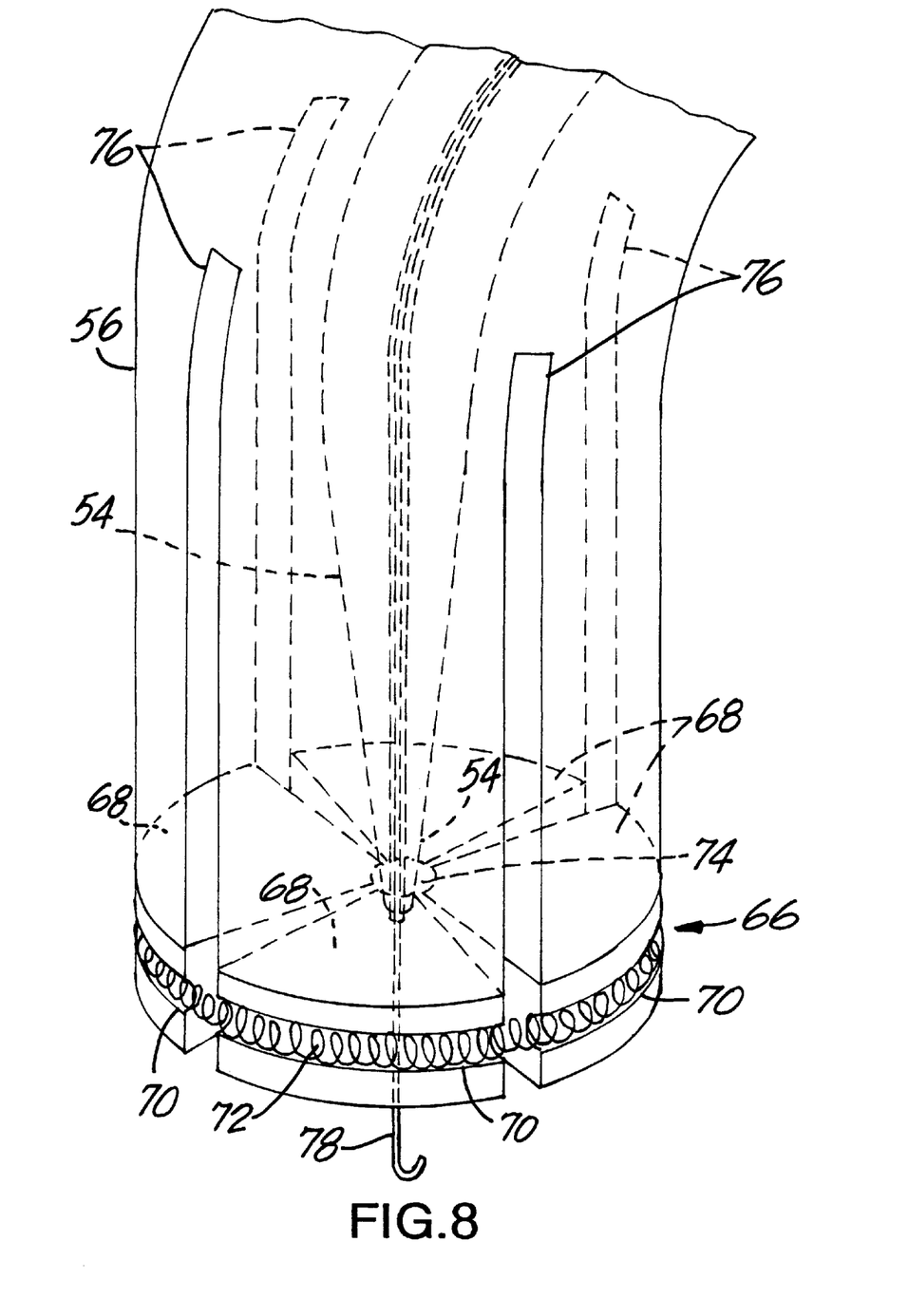
FIG. 8 is a perspective view of the lower end of the sizing catheter according to the present invention.

A view of the lower end of the sizing catheter is shown in FIG. 8. The expandable member 66 is preferably of a cylindrical configuration including four separate plates 68 arranged substantially in a co-planar configuration. The plates 68 are attached to an inner surface of the outer catheter 56 and include an opening 74 at the center. During operation, the tapered end 54 is advanced within the opening 74 in order to outwardly expand the plates 68.

In order to make an accurate measurement, the outward expansion of the plates 68 must be somehow related to the advancement of the tapered end 54, which corresponds to the diameter indicated in the scale. This can be accomplished by configuring the tapered end 54 to provide a predetermined amount of expansion per unit of advancement. Such a configuration can be calculated by the trigonometric relationship between the length and radius of the tapered end 54.

As can be further seen, each of the plates 68 include a groove 70 on a side surface. A spring 72 is disposed within the grooves 70, which enables the spring to be secured around the side surface of the expandable member 66. The spring 72 maintains the plates 68 in an unexpanded position when the tapered end 54 of the inner catheter is not being advanced.

The outer catheter 56 at the lower end also preferably includes four longitudinal slits 76 aligned with the spaces between the plates 68. The longitudinal slits 76 also enable the plates 68 to gradually expand outward when the tapered end 54 is advanced, which as previously described is desirable since it provides a more accurate measurement.

In performing a measurement, the expandable member 66 operates as follows. The tapered end 54 of the inner catheter will be advanced within the opening 74, which causes the plates 68 to gradually expand outward. As previously described, at the point where the side surfaces of the plates 68 contact the inner wall of the vein, there is resistance to further advancement of the inner catheter 44. At this point, the diameter is indicated on the scale. After the measurement is performed, the tapered end 54 of the inner catheter is withdrawn and the spring 72 returns the plates 68 to the unexpanded position.

According to the present invention, the sizing catheter 42 can be utilized in a venous valve placement procedure as follows:

a. Perform percutaneous puncture of the vein such as a Jugular vein, Subclavian vein, Arm vein, Femoral vein or Popliteal vein.

b. Under fluoroscopy insert a guidewire 78 through the needle and advance the guidewire beyond the proposed site of valve placement.

c. Make a small stab incision in the skin at the exit point of the guidewire 78. Insert a dilator and sheath over the guidewire. (These are standard devices in current use for inserting large catheters into the venous system).

d. Remove the dilator, leaving the guidewire 78 and sheath in place. Pinch the sheath with the fingers to prevent back bleeding.

e. The sizing catheter 42 is flushed with heparin solution before performing the percutaneous puncture described above. Now insert the catheter 42 over the guidewire 78 into the sheath. Advance the tip of this catheter 42 to the incompetent vein.

f. Inject dye to obtain a venogram. Mark the proposed site of valve placement by attaching a radioopaque ruler, or any metallic marker, such as a clamp, to the sterile drapes. If more than one valve is to be placed in an extremity, the distal valve must be placed first.

g. Under fluoroscopy advance the tip (radioopaque) of the catheter 42 to the proposed site of valve placement. Measure the diameter of the vein at this site by advancing the inner catheter 44 up to the point of resistance. The diameter of the blood vessel is read from the scale 46 on the inner catheter 44. If needed, venography can be preformed through this catheter 44 to confirm proper sizing.

h. Remove the catheter 42 leaving the guidewire 78 and sheath in place.

i. Remove all blood from the catheter 42 by flushing with heparin solution.

j. Insert a valve carrier including the artificial venous valve of appropriate size over the guidewire into the sheath and advance the tip to the marker for the proposed site of valve placement.

k. Release the valve into the vein by loosening the safety screw 34 and pushing the plunger 38.

l. Withdraw the valve carrier and the guidewire for a short distance to a position proximal to the valve.

m. Perform a venogram to confirm proper placement and function of the valve.

n. To place additional valves remove the valve carrier leaving the guidewire and sheath in place.

o. Insert the sizing catheter 42 over the guidewire 78 through the sheath. Advance the tip to the incompetent vein.

p. Repeat steps f to m.

q. Remove the valve carrier, sheath and guidewire 78.

r. Apply pressure over the puncture site to ensure hemostasis.

There has been disclosed heretofore the best embodiment of the invention presently contemplated. However, it is to be understood that various changes and modifications may be made thereto without departing from the spirit of the invention.

What is claimed is:

1. A self-expanding, self-attaching venous valve device for percutaneous insertion into a body cavity, comprising:
    a valve ring having a compressible diameter biased toward an expanded position; and
    leaflets hingedly and pivotally disposed within said valve ring for movement from an open position to a closed position.

2. The device of claim 1, wherein said valve ring includes a first plurality of arcuate tubes and a second plurality of arcuate tubes telescopically disposed in said first tubes.

3. The device of claim 2, which further includes a spring disposed in each of said first tubes between two of said second tubes.

4. The device of claim 2, wherein said second tubes at each end include projections extended outward, said first tubes include at each end includes a lip extending inward, wherein said projections engage said lip in order to prevent disconnection of the first and second tubes.

5. The device of claim 4, wherein said projections are spring loaded.

6. The device of claim 2, wherein said leaflets include ridges on an underside to provide a seal between said leaflets and said second tubes.

7. The device of claim 1, wherein said valve ring includes grooves for applying a radial force to compress said compressible diameter.

8. The device of claim 1, further including barbs extending outward from said valve ring.

9. The device of claim 1, wherein each of said leaflets are pivotally connected to said valve ring by an unbiased hinge having a peripheral axis.

10. The device of claim 1, wherein said expanded position of said compressible diameter is predetermined prior to percutaneous insertion.

11. The device of claim 1, wherein said valve ring is fully expanded to the diameter of the body cavity in a resting position.

12. A catheter device for percutaneous insertion into a body cavity, comprising:
    a first catheter;
    an expandable member disposed at a lower end of said first catheter and inside said first catheter;
    a second catheter disposed within said first catheter; and
    a scale included on said device;
    wherein said second catheter being advanced within said first catheter causes said expandable member to move to an expanded position, wherein said expanded position corresponds to a diameter measurement on said scale.

13. The device of claim 12, wherein said second catheter includes a tapered lower end.

14. The device of claim 13, wherein said tapered lower end has an elongated conical shape.

15. The device of claim 12, wherein said expandable member has a cylindrical configuration.

16. The device of claim 12, wherein said expandable member includes separate plates.

17. The device of claim 16, wherein said plates are four separate plates.

18. The device of claim 16, wherein said plates are attached to said inner surface of said first catheter.

19. The device of claim 16, wherein said plates are arranged in a substantially co-planar arrangement.

20. The device of claim 16, which further includes a spring disposed around outer edges of said plates.

21. The device of claim 20, wherein said outer edges of said plates include a groove in order to receive said spring.

22. The device of claim 12, wherein said first catheter includes longitudinal slits.

23. The device of claim 22, wherein said longitudinal slits are aligned with spaces between said plates.

24. The catheter device of claim 12, wherein said scale is provided on said second catheter.

25. A venous valve device for percutaneous insertion into a body cavity, comprising:
    a valve ring having a compressible diameter biased toward an expanded position, leaflets pivotally disposed within said valve ring for movement from an open position to a closed position, wherein said valve ring includes a first plurality of arcuate tubes and a second plurality of arcuate tubes telescopically disposed in said first tubes, and wherein said second tubes at each end include spring loaded projections extended outward, said first tubes include at each end a lip extending inward, wherein said projections engage said lip in order to prevent disconnection of said first and second tubes.

26. A catheter device, comprising:

a first catheter;

an expandable member disposed at a lower end of said first catheter and further comprising separate plates attached to an inner surface of said first catheter;

a second catheter disposed within said first catheter; and a scale included on said device;

wherein said second catheter being advanced within said first catheter causes said expandable member to move to an expanded position, wherein said expanded position corresponds to a diameter measurement on said scale.

27. A catheter device, comprising:

a first catheter;

an expandable member disposed at a lower end of said first catheter, said expandable member further comprising separate plates attached to an inner surface of said first catheter and a spring disposed around outer edges of said plates;

a second catheter disposed within said first catheter; and a scale included on said device;

wherein said second catheter being advanced within said first catheter causes said expandable member to move to an expanded position, wherein said expanded position corresponds to a diameter measurement on said scale.

* * * * *